United States Patent [19]

Sheehan et al.

[11] 4,282,149

[45] Aug. 4, 1981

[54] CARBON AND OXYGEN ANALOGS OF PENICILLIN

[75] Inventors: John C. Sheehan, Lexington; Young S. Lo, Boston, both of Mass.

[73] Assignee: Massachusetts Institute of Technology, Cambridge, Mass.

[21] Appl. No.: 946,438

[22] Filed: Sep. 27, 1978

Related U.S. Application Data

[60] Division of Ser. No. 779,828, Mar. 21, 1977, Pat. No. 4,143,046, which is a continuation of Ser. No. 347,772, Apr. 4, 1973, abandoned.

[51] Int. Cl.$^3$ ............................................. C07D 499/00
[52] U.S. Cl. ................................ 260/245.2 R; 424/270
[58] Field of Search .......................... 260/306.7, 245.2; 424/270, 271

[56] References Cited

U.S. PATENT DOCUMENTS

| | | | |
|---|---|---|---|
| 3,159,617 | 12/1964 | Sheehan | 260/239.1 |
| 3,681,380 | 8/1972 | Cooper et al. | 260/306.7 C |
| 3,720,664 | 3/1973 | Erickson et al. | 260/239.1 |
| 3,720,666 | 3/1973 | Sellseept | 260/239.1 |
| 3,796,641 | 8/1976 | Hoover | 260/243 R |
| 3,799,939 | 3/1974 | Rapoport | 260/306.7 C |
| 3,809,700 | 5/1974 | Rapoport | 260/306.7 C |
| 4,053,408 | 10/1977 | Holden | 260/243 C |
| 4,093,625 | 6/1978 | Commons et al. | 260/306.7 |

OTHER PUBLICATIONS

Barton et al., Proc. R. Soc. Lond B. 179, 345–355 (1971).
Gutowski, Tetrahedron Letters No. 21 pp. 1779–1782 (1970).
Vedejs et al., Tetrahedron Letters No. 2 pp. 1863–1864 (1970).
Reiner et al. Helvetica Chimica Acta 51 Fasc 8 pp. 1905–1908, (1962).
Hauser et al., Helv Chim Acta 50 Fasc 5 No. 135 pp. 1327–1335 (1967).
Pfitzner et al. Jacs 85 3027 (1963).
Lo et al., Jacs 94 8253 (1972).
Lo et al., Jorg Chem. 40 191 (1975).
Sheehan, The Synthetic Penicillins Advancer in Chemistry Series No. 45 pp. 15–24 (1964).
Simon, The Total Synthesis of Natural Products vol. 1 1974 p. 337–338 Wiley Interscience.
Clayton et al. J. Chem. Soc. 2123 (1969).
Heusler, Total Synthesis of Pencillins and Cephalosporins.
Cephalosporins and Penicillins, edited by E. Flynn pp. 96–105 (Kaiser et al.) 1972.

*Primary Examiner*—Nicholas S. Rizzo
*Attorney, Agent, or Firm*—Arthur A. Smith, Jr.; George W. Neuner; David G. Conlin

[57] ABSTRACT

In accordance with this invention, it has been found that carbon and oxygen analogs of 6β-aminopenicillanic acid and biologically active derivatives thereof can be formed from esters of 6-oxopenicillanic acid. For example, 6β-phenoxyacetoxy-penicillanic acid—an oxygen analog of penicillin V and 6β-phenoxyacetylmethyl-penicillanic acid—a carbon analog of penicillin V, may be formed from an ester of 6-oxopenicillanate. The ester of 6-oxopenicillanic acid is formed by a diiospropyl carbodiimide/dimethyl sulfoxide oxidation of the corresponding ester of 6α-hydroxypenicillanic acid. The oxygen analogs are formed by reducing the ester of 6-oxopenicillanic acid to the corresponding 6β-hydroxypenicillanate and then forming the desired analog by acylation. The carbon analogs are formed by a Wittig reaction of the ester of 6-oxopenicillanic acid with a suitable acylmethylenetriphenylphosphorane followed by saturation of the newly formed double bond and removal of the protective ester group.

32 Claims, No Drawings

CARBON AND OXYGEN ANALOGS OF PENICILLIN

This is a division of application Ser. No. 779,828 filed Mar. 21, 1977 U.S. Pat. No. 4,143,046 which is a continuation of Ser. No. 347,772 filed Apr. 4, 1973 now abandoned.

BACKGROUND OF THE INVENTION

1. Introduction

This invention relates to derivatives of penicillin and more particularly to carbon and oxygen analogs of 6-aminopenicillanic acid and biologically active derivatives thereof.

2. Description of the Prior Art

In U.S. Pat. No. 3,159,617, there is taught the first commercial synthesis 6-aminopenicillanic acid and penicillin derivatives based thereon. A vast number of derivatives of the 6-aminopenicillanic acid may be formed by introduction of various groups into the amino group of the acid. Thus, acyl groups, isocyanates, isothiocyanates, halogen compounds, methylisoureas, ethylene oxide, ethylene imine, and the like have been introduced into the amino group of the 6-aminopenicillanic acid to form both biologically active and biologically inactive derivatives.

Many of the derivatives of 6-aminopenicillanic acid, especially those derivatives formed by acylation have become useful drugs. For example, ampicillin and carbenicillin have broadened the spectra of activity to include use against certain Gram-negative organisms while methicillin shows good activity against certain resistant staphylococci.

In an effort to find new biologically active derivatives of 6-aminopenicillanic acid, attempts have been made to modify the same by methods in addition to introduction of new groups into the amino group. Thus, stimulated by the elucidation of the structure of the cephalosporins, there have been attempted modifications of the thiazolidine moiety of 6-aminopenicillanic acid. This is especially true since cephalosporins are not readily available from nature and most of the drugs used today are converted from penicillins. Thus, much effort has been concentrated on the investigation of possible transformations of the thiazolidine ring to the dihydrothiazine ring without any concomitant change of the chemically sensitive $\beta$-lactam moiety. These efforts are described by D. H. R. Barton and T. G. Sammes, Proc. R. Soc. Lond. B, 179, 345 (1971).

Other attempts have been made to modify 6-aminopenicillanic acid through modification of the $\beta$-lactam moiety, but such attempts are relatively few and are focused on the variations on the substituents or stereochemistry of the C-6 carbon in the penam system. Primarily, four types of modifying reactions are reported, namely acylation, epimerization, alkylation and diazotization.

One successful example of the epimerization reaction is reported by G. E. Gutowski, Tet lett., 1970, 1779 and 1863. However, this penicillin having the epimerized C-6 substituent is devoid of any biological activity. With regard to alkylation at the C-6 position, most attempts have been to introduce an $\alpha$-alkyl group based upon earlier predictions that the introduction of an $\alpha$-methyl group at the C-6 position might enhance antibiotic activity. Both direct and indirect $\alpha$-hydroxyalkylation of the penicillin nucleus at C-6 with benazldehyde and formaldehyde is reported by R. Riner and P. Zeller, Helv Chim. Acta 51, 1905 (1968). These derivatives and other $\alpha$-alkylated derivatives show some biological activity, but both show substantially less activity than the well known penicillin G. Deamination of 6-aminopenicillanic acid by sodium nitrite in mineral acid proceeds with the inversion at C-6 resulting in the C-5 and C-6 protons being trans-oriented in the product. When the reaction is run in the presence of a halo acid, a 6-$\alpha$-halo product is obtained. Deamination of 6-aminopenicillanic acid by sodium nitrite with oxygen acids is reported by T. Hauser and H. P. Sigg, Helv, Chim, Acta, 50, 1327 (1967). With such oxygen acids, 6$\alpha$-hydroxypenicillanic acid is isolated as the benzyl ester which may then be transformed to the $\alpha$-oxygen analog 6-$\alpha$-phenoxyacetoxypenicillanic acid, the $\alpha$-oxygen analog of penicillin V. This material shows no biological activity.

SUMMARY OF THE INVENTION

The present invention is based upon the discovery that though the aforementioned ester of 6$\alpha$-hydroxypenicillanic acid is biologically inactive, it can be transformed to an ester of 6-oxopenicillanic acid which latter ester can be transformed to carbon and oxygen analogs of 6-$\beta$-aminopenicillanic acid. These analogs are biologically active as are the derivatives of these analogs.

The ester of the 6-oxopenicillanic acid is formed by diisopropyl carbodiimide/dimethyl sulfoxide oxidation of the corresponding, biologically inactive, ester of 6$\alpha$-hydroxypenicillanic acid. The oxygen analogs are formed by reducing the ester of the 6-oxopenicillanic acid to the corresponding 6$\beta$-hydroxypenicillanate and then to the desired derivative by a reaction such as acylation in a manner analogous to the acylation of 6-aminopenicillanic acid. The carbon analogs are formed by a Wittig reaction of an ester of 6-oxopenicillanic acid with a suitable acylmethylenetriphenylphosphorane followed by saturation of the newly formed double bond and removal of the protective ester group.

DESCRIPTION OF THE PREFERRED EMBODIMENT

As noted above, 6-$\alpha$-hydroxypenicillanic acid is formed by deamination of 6$\beta$-aminopenicillanic acid with sodium nitrite and certain acids such as perchloric acid or sulfonic acid according to the process of Hauser and Sigg. ibid. The 6$\alpha$-hydroxypenicillanic acid, which is biologically inactive, is isolated as an ester. Preferably, the benzyl ester is formed by reaction with phenyldiazomethane, though any other ester providing a pharmaceutically useful blocking group may be used provided the group is readily removed. Using the benzyl ester for purposes of illustration only, this ester of 6$\alpha$-hydroxypenicillanic acid is then oxidized to benzyl 6-oxopenicillanate by diisopropylcarbodiimide in dimethylsulfoxide according to the procedures described by K. E. Pfitzner and J. G. Moffatt, Journal of American Chemical Society, 85, 3027, (1963). It is this material which is the starting material for the formation of carbon and oxygen analogs of 6$\beta$-aminopenicillanic acid and the biologically active derivatives thereof.

As noted above, the aforesaid reaction for the formation of the benzyl 6-oxopenicillanate may be used for the formation of other esters of 6-oxopenicillanic acid and in this respect, for purposes of this invention, the general formula for the ester of the 6-oxopenicillanic acid is as set forth below:

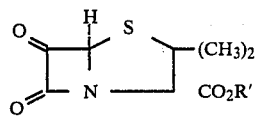

where R' represents a pharmaceutically useful or readily removable protective group. Such groups include (1) alkyl, cycloalkyl, aryl, alkaryl and aralkyl as illustrated by methyl, benzyl and $\beta,\beta,\beta$-trichloroethyl, (2) phenacyl with or without substitution on the ring such as p-methoxyphenacyl and 2,5-dimethoxyphenacyl, (3) salts such as sodium, potassium, N-ethylpiperidine and dicyclohexylamine and (4) organo silicon groups such as trimethyl silyl, it should be understood that some of the aforesaid groups may be more difficult to remove than others, but most are groups heretofore used as protective groups in analogous reactions of penicillins and are removed in accordance with recognized procedures dependent upon the particular group involved.

The aforesaid ester of 6-oxopenicillanic acid (I) is the starting material for the formation of the oxygen analogs of 6$\beta$-aminopenicillanic acid and the derivatives thereof. The principles of the reaction scheme for the formation of the oxygen analog as well as derivatives thereof are illustrated in the following reaction chart. In the specific example referred to in this chart, there is described for purposes of illustration only, the production of the oxygen analog of penicillin V (phenoxymethylpenicillin) from benzyl 6-oxopenicillanate:

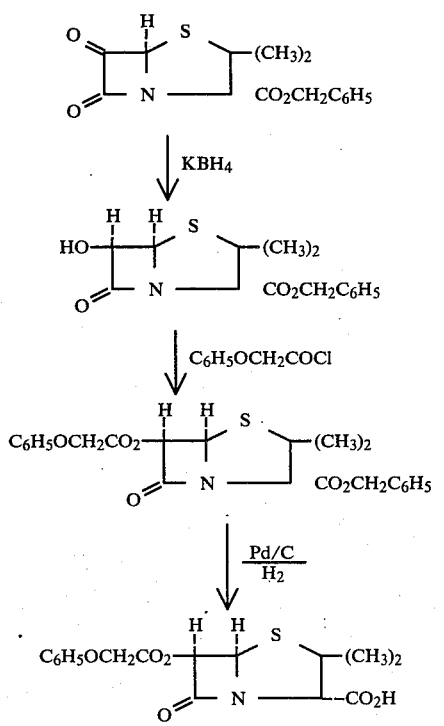

In the above reaction sequence, the benzyl 6-oxopenicillanate (II) is reduced to benzyl 6$\beta$-hydroxypenicillanate (III) with potassium borohydride. This material shows biological activity which is quite unexpected as it is the epimer of the corresponding benzyl 6-$\alpha$-hydroxypenicillanate which shows no biological activity. Though not shown in the reaction chart, this material can be transformed to 6$\beta$-hydroxypenicillanic acid by hydrogenolysis over a palladium catalyst to remove the benzyl group and give the free acid as represented by the following formula:

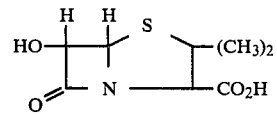

This material is the oxygen analog of 6$\beta$-aminopenicillanic acid and is also biologically active.

Following further in the above reaction chart, the benzyl 6$\beta$-hydroxypenicillanate (III) is phenoxyacetylated to give benzyl 6$\beta$-phenoxyacetoxypenicillanate (IV). Hydrogenolysis over a palladium catalyst to remove the benzyl group gives the free acid (V) which material is considered to be the oxygen analog of penicillin V. In proceeding from the benzyl 6-oxopenicillanate, it should be noted that it was not necessary to go through the oxygen analog 6$\beta$-hydroxypenicillanic acid (VI) though this may be done, if desired.

From the foregoing reaction chart, it can be seen that organic acid radicals can be introduced into the hydroxyl group of the benzyl 6$\beta$-hydroxylpenicillanate (III) or 6$\beta$-hydroxylpenicillianic acid (VI), as illustrated by the phenoxyacetylation step in a manner analogous to the reactions of the amino group of 6-aminopenicillanic acid. A wide variety of acyl groups can be introduced into the hydroxyl group thus making it possible to produce a wide variety of oxygen analogs of penicillin. In this respect, typical acylating agents include for example, formyl, acetyl, phenylacetyl, phenoxyacetyl, carbomethoxy, carbobenzyloxy, p-nitrocarbobenzyloxy, carbophenoxy, p-chlorocarbophenoxy, methanesulfonyl, benzylsulfonyl, p-chlorobenzylsulfonyl, phenylsulfonyl, p-aminophenylsulfonyl or N,N-pentamethylenesulfonyl. Although the halides, especially chlorides and bromides, or anhydrides of the acid group to be introduced into the 6$\beta$-hydroxypenicillanic acid are particularly suitable, other acylating agents may also be used. Such acylating agents include mixed anhydrides, acid azides, lactones, particularly $\beta$-lactones, "activated esters" such as thiol esters and phenolic esters, carboxylic acids with carbodiimides or alkoxyacetylenes, thiolactones, particularly $\beta$-thiolactones, and acylated enols.

Other groups can also be introduced into the hydroxy group of 6$\beta$-penicillanic acid to provide additional types of penicillin analogs by means of such reagents as: isothiocyanates, for example, phenylisothiocyanate and ethylisothiocynate, to convert the hydroxy group to a substituted thioncarbonate, reactive halogen compounds, such as triphenylmethyl chloride which forms the trityl ether derivative; methylisourea which converts the hydroxyl group to an isourea group; ethylene oxide and ethyleneimine, which add to the hydroxyl group with ring opening and others known to the art. Further exemplification of the above and, additional groups can be found by reference to Naylor, Proc. R. Soc. Land, B 179, pp. 357–367, 1971, wherein the reactions of 6-aminopenicillanic acid are described in detail.

With further reference to the above reaction scheme, it should be noted that the free acid 6$\beta$-phenoxyacetoxypenicillanic acid (V) can be esterified in conventional manner to further alter the structure of the derivatives such as by formation of the methyl ester by reaction with diazomethane. Thus, by selection of the appropriate acylating agent for reaction with the benzyl 6β-hydroxypenicillanate (IV) and by selection of an appropriate material to react with the free acid (V) or by a combination of such reactions with the oxygen analog 6β-hydroxypenicillanic acid (VI), a multitude of derivatives of the oxygen analogs can be formed having the formula:

(VII)

where R' is as above defined and R'' may be selected from the group of (1) organic carboxylic radicals such as phenylacetyl, phenoxyacetyl, 2,6-dimethoxybenzoyl, α-carboxyphenylacetyl, α-aminophenylacetyl and tyrosyl, (2) an organic carbonic acid radical such as carbomethoxy, carbobenzyloxy and carbo β,β,β-trichloroethoxy, and (3) an organic sulfonic acid radical.

The ester of 6-oxopenicillanic acid (I) is also the starting material for the formation of the carbon analogs in accordance with the invention. These carbon analogs are formed by a Wittig reaction of the ester with an acylmethylenetriphenylphosphorane of the formula:

$$(C_6H_5)_3P=CHR_1 \quad \text{(VIII)}$$

where $R_1$ is selected from the group consisting of H and R'' where R'' is as defined above. The formation of Wittig reagents is described in Organic Reactions, 14, pp. 270–490.

The principles for the reaction scheme for the formation of the carbon analog as well as derivatives thereof are illustrated in the following reaction chart. In the specific example referred to in the chart, there is described for purposes of illustration only, the production of the carbon analog of penicillin V (phenyoxymethylpenicillin) from benzyl-6-oxopenicillanate.

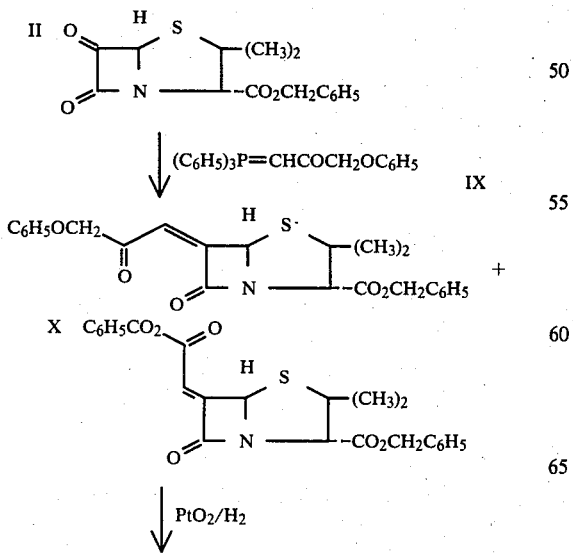

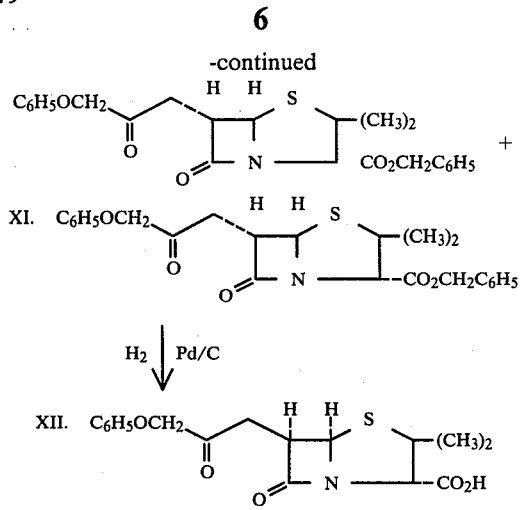

In the above reaction sequence, the benzyl 6-oxopenicillinate (II) is subjected to a Wittig reaction with a phenoxyacetylmethylenetriphenylphosphorane (IX) to give benzyl 6β-phenoxyacetylmethylenepenicillanate (X). It is suspected that the product is a mixture of geometrical isomers and the saturated isomers are obtained by hydrogenation over platinum oxide. The 6β-phenoxyacetylmethylpenicillanic acid (XII) is obtained by hydrogenolysis of the benzyl 6β-phenoxyacetylmethylpenicillanate (XI) over palladium on charcoal. This material is the carbon analog of penicillin V.

With respect to the 6β-phenoxyacetylmethylpenicillanic acid (XII) the acid radical is reactive and can be used to form additional derivatives. Moreover, since there is the possibility for selection for substitution on the 6-C position dependent upon the selection of the Wittig reagent, a derivative of a carbon analog of 6β-aminopenicillanic acid can be formulated having the following general formula:

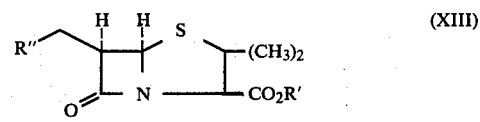
(XIII)

where R' and R'' are as defined above.

The carbon analog of 6-aminopenicillanic acid may be formed by the following reaction sequence:

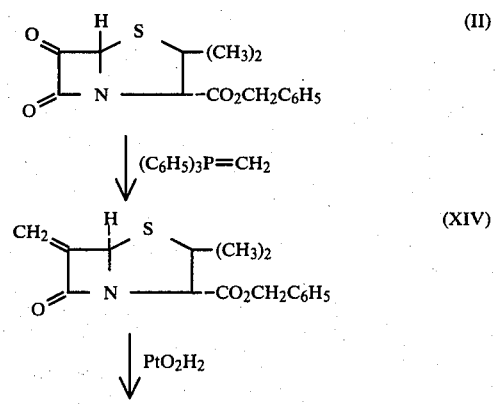

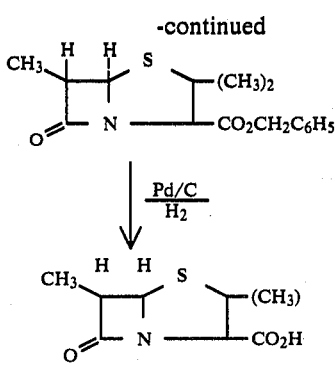

The above free acid (XVI) is the carbon analog of 6-aminopenicillanic acid. It can be reacted such as by esterification to form derivatives corresponding to the formula:

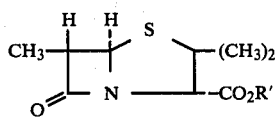

where $R^1$ is as above defined.

The following examples will help to illustrate the invention with more particularity.

Benzyl 6α-hydroxypenicillanate

This compound was prepared by the method of Hauser and Sigg. The crude product was recrystallized in benzene; mp 162°–163° (lit. 157°–160°); $\alpha_D{}^{25} = +200°$ (c=0.62, MeOH) (lit. +191° (c=0.53, MeOH); ir and nmr spectra are identical to those published.

Benzyl 6-oxopenicillanate

Pfitzner and Moffatt's DMSO oxidation method, ibid, was employed to transform the benzyl 6α-hydroxypenicillanate to benzyl 6-oxopenicillanate. Thus, benzyl 6α-hydroxypenicillanate (9 g, 29.30 mmol) was dissolved in 120 ml dimethyl sulfoxide. Pyridine (2.37 ml, 29.30 mmol) and trifluoroacetic acid (1.10 ml, 14.65 mmol) were added. To the stirred solution, N,N$^1$-diisopropylcarbodiimide (11.30 g, 87.90 mmol) was added slowly and the stirring continued for 17 hours. Distilled water (23 ml) was added dropwise to the stirred reaction mixture to consume the excess carbodiimide. The resulting mixture was filtered to remove the solid N,N$^1$-diisopropylurea. To the filtrate was added 800 ml benzene, and the solution was washed with three 800 ml portions of water to remove dimethyl sulfoxide. The resulting benzene solution was dried over anhydrous sodium sulfate. After evaporation of benzene, the yellow residual oil partly solidified when stored in vacuum. It contains 54% of benzyl 6-oxopenicillanate as determined by the formation of its cyanohydrin. This crude product was used without purification in the subsequent transformations.

However, pure benzyl 6-oxopenicillanate can be isolated by two successive column chromatographic separations. First, 4 g crude reaction product were chromatographed on a silicic acid column (200 g) which was eluted with an excess methylene chloride (1400 ml) to remove most of the diisopropylurea and other contaminants. Then the eluting solvent was changed to 1:4 $Et_2O/CH_2Cl_2$ to wash out the partially purified benzyl 6-oxopenicillanate (2.59).

The product (1 g) was further purified on a second column of silicic acid (50 g) using 1:25 $Et_2O/CH_2Cl_2$ as eluent. Fractions (8 ml) were collected and checked by TLC. Fractions 31 to 50 were combined and the solvent evaporated. The residual yellow oil solidified after evaporation at 1 mm Hg to give 0.5 g of the benzyl 6-oxopenicillanate; $R_f$=0.19 (1:25 $Et_2O/CH_2Cl_2$); $[\alpha]_D{}^{25} = +186°$ (c=0.92, $C_6H_6$); ir (film, cm$^{-1}$) 1830, 1780, 1735; nmr (DCCl$_3$, ppm) 7.40 (s, 5H), 5.85 (s, 1H), 5.30 (s, 2H), 4.87 (s, 1H), 1.55 (s, 3H), 1.48 (s, 3H). Anal. Calcd for $C_{15}H_{15}NO_4S$ (305.40): C, 59.10; H, 4.96; N, 4.59; S, 10.50. found C, 58.97; H, 5.07; N, 4.53; S, 10.60.

Benzyl 6β-hydroxypenicillanate

To a cooled, stirred solution of crude benzyl 6-oxopenicillanate (8.15 g, 14.48 mmol) in 470 ml 1:1 methanol/ethanol was added a cold solution of potassium borohydride (0.85 g, 15.75 mmol) in 570 ml 50% aqueous ethanol. After two minutes, 1 N hydrochloric acid was added to bring the pH of the solution to 2. The solution was extracted twice with methylene chloride and the combined extracts were washed once with 5% sodium bicarbonate solution, once with water, dried over anhydrous sodium sulfate, and evaporated at reduced pressure. The resulting yellow oil was chromatographed on a silicic acid column eluted with 1:4 $Et_2O/CH_2Cl_2$ to isolate benzyl 6β-hydroxypenicillanate which was recrystallized from benzene-pentane to yield 2.80 g (63%); mp 97°; $[\alpha]_D{}^{25} = +222°$ (c=0.87, MeOH); ir (KBr, cm$^{-1}$) 3420, 1780, 1725; nmr (DCCl$_3$, ppm) 7.36 (s, 5H), 5.56 (d,1H, J=4), 5.20 (s, 2H), 5.22–4.98 (q, 1H, J=4 and 11), 4.50 (s, 1H), 3.40–3.20 (d, br, 1H, J=11), 1.65 (s, 3H), 1.50 (s, 3H).

Anal. Calcd for $C_{15}H_{17}O_4NS$ (307.40): C, 58.80; H, 5.20; N, 4.60; S, 10.40. Found. C, 58.73; H, 5.32; N, 4.48; S, 10.20.

Benzyl 6β-phenoxyacetoxypenicillanate

Benzyl 6β-hydroxypenicillanate (1.26 g, 4.11 mmol) was phenoxyacetylated in methylene chloride (120 ml) with phenoxyacetyl chloride (0.97 g, 5.71 mmol) and triethylamine (0.77 ml, 5.56 mmol) for 3 hours. Excess reagents were removed by washing with 1 N potassium bicarbonate and water. Evaporation of the solvent yielded a yellow oil, 1.90 g. Purification by chromatography on silicic acid eluted with 1:50 $Et_2O/CH_2Cl_2$ gave a pale yellow oil; 1.55 g (85%); $R_f$=0.43 (1:50 $Et_2O/CH_2Cl_2$); $[\alpha]_D{}^{25} = +210°$ (c=1.06, CHCl$_3$); ir (film, cm$^{-1}$) 1780, 1740, 1600, 1500; nmr (DCCl$_3$, ppm) 7.35 (s, 5H), 7.40–6.70 (m, 5H), 5.80–5.60 (q,2H, J=4), 5.25 (s, 2H), 4.70 (s, 2H), 4.55 (s,1H), 1.60 (s, 3H), 1.45 (s,3H).

Anal. Calcd for $C_{23}H_{23}O_6NS$ (441.39): C, 62.75; H, 5.27 N, 3.19; S, 7.26; Found: C, 62.50; H, 5.40; N, 3.12; S, 7.46.

6β-Phenoxyacetoxypenicillanic acid

Benzyl 6β-phenoxyacetoxypenicillanate (0.81 g, 1.84 mmol) dissolved in 120 ml ethyl acetate was hydrogenated over 10% palladium on charcoal (4 g) for 11 hours at room temperature and 1 atm.pressure. The resulting mixture was filtered to remove the catalyst and the filtrate was extracted twice with 50 ml portions of cold 1 N potassium bicarbonate solution. The combined aqueous extracts were washed once with ether and cooled to 0°. Ether was added and the stirred mixture was acidified to pH 2 by slow addition of concentrated hydrochloric acid (12 N). The ether layer was separated and the aqueous layer was extracted three times with ether. The organic phase was then washed once with distilled water, dried over anhydrous sodium sulfate and evaporated to yield a pale yellow oil, 0.53 g. This oil was obtained as a white solid, 0.48 g, after freeze drying from benzene. The product absorbed moisture readily from the air and after attempted recrystallization, the yellow oil was recovered. TLC showed two spots with heavy tailing, $R_f=0.50$ and 0.22 (1:4 Et$_2$O/CH$_2$Cl$_2$); ir (CH$_2$Cl$_2$, cm$^{-1}$) 3620, 3440, 1790, 1765, 1745, 1720, 1595, 1490, nmr (DCCl$_3$,ppm) 8.90 (s, 2H), 7.50–6.80 (m, 8H), 5.90–5.60 (q, 2H, J=4), 5.35–5.25 (m, br, 0.5H), The singlet at 4.70 ppm is believed to be the α-protons of phenoxyacetic acid which is present as a side-product of hydrogenolysis. From the integration, the ratio of 46a to phenoxyacetic acid is 2 to 0.9.

Potassium Salt

The free acid formed above (0.22 g, 0.63 mmol) was dissolved in a mixture of 10 ml ethyl ether and 20 ml distilled water. The stirred mixture was titrated with 0.1 N potassium hydroxide solution at 0° to pH 7.5 as indicated by a pH meter. The aqueous phase was separated and washed once with ethyl ether. The solution was reduced at room temperature to about 8 ml and freeze dried to give a white solid, 0.26 g. The salt was insoluble in benzene, chloroform, ethyl ether, ethyl acetate, acetone, and tetrahydrofuran. Recrystallization from acetone-water failed and the substance was recovered by freeze drying; mp 180°; ir (KBr, cm$^{-1}$), 3540–3040, 1770–1720, 1590; nmr of the salt in D$_2$O showed weak signals for the compound among other impurity signals (ppm) 7.60–6.90 (m, 9H), 5.90–5.60 (q, 2H), 4.90 (s, 1.5H), 4.80 (s, strong water peaks with side bands), 4.47 (s, 2H), 4.32 (s, 1H), 2.73 (s, 2H), 2.30 (s, 3.6H), 1.60–1.55 (d, 6H), 1.30 (s, 6.2H). The compound exhibits low bacteriostatic endpoints (in mcg. of active material per ml) for pneumoniae (5% serum), *Streptococcus pyogenes* (5% serum), and *Staphylococcus aureas*.

Methyl 6β-phenoxyacetoxypenicillanate

Crude potassium 6β-phenoxyacetoxypenicillanate (0.27 g, 0.69 mmol) was reconverted to the free acid by acidifying the aqueous solution covered with ethyl ether at 0° with N hydrochloric acid. Worked up as described above, 0.23 g (95%) free acid was obtained as an oil which was then methylated with diazomethane in ether solution to give 0.24 g yellow oil. After separation by a silicic acid column eluted with 1:25 Et$_2$O/CH$_2$Cl$_2$, methyl phenoxyacetate was isolated from early fractions as a colorless oil, 0.08 g; ir (film cm$^{-1}$) 1755, 1600, 1495, 1440, 1290, 1200, 1090; nmr (DCCl$_3$, ppm) 7.50–6.85 (m, 5H), 4.65 (s, 2H), 3.80 (s, 3H).

The later fractions gave 0.15 g of methyl 6β-phenoxyacetoxypenicillinate as a colorless oil which was rechromatographed to give 0.12 g (48%); $R_f=0.46$ (1:25 Et$_2$O/CH$_2$Cl$_2$); $[\alpha]_D^{25}=+268°$ (c=0.97, CHCl$_3$); ir (film, cm$^{-1}$) 1790, 1740, 1600, 1495, 1310, 1210, 1170; nmr (DCCl$_3$, ppm) 7.50–6.85 (m, 5H), 5.90–5.65 (q, 2H, J=3.5), 4.80 (s, 2H), 4.55 (s, 1H), 3.80 (s, 3H), 1.60 (s, 3H), 1.50 (s, 3H).

Anal. Calcd for C$_{17}$H$_{19}$O$_0$NS (365.39): C, 58.65; H, 5.25; N, 3.84; S, 8.79. Found: C, 58.50; H, 5.47; N, 3.79; S, 8.85.

6β-Hydroxypenicillanic acid and methyl ester

Benzyl 6β-hydroxypenicillanate (1.31 g, 4.27 mmol) was dissolved in 150 ml ethyl acetate and hydrogenated over 10% palladium on charcoal (2.5 g) for 24 hours at room temperature. The hydrogen pressure was maintained at 50 psi for the first two hours. At the end of the reaction period, it had fallen to 42.5 psi. The free acid was isolated as described for the preparation of 6β-phenoxyacetoxypenicillanic acid to give 0.61 g (66%) of a white solid. From the organic layer, 0.44 g (34%) of benzyl 6β-hydroxypenicillanate was recovered. The white solid thus obtained had mp 130° (dec. begins); ir (KBr, cm$^{-1}$) 3560–2480, 1775, 1725; nmr in acetone-d$_6$ showed broad peaks at (ppm) 5.60–5.10, 4.45, 3.90–3.60, 1.80–1.65, 1.40–1.25. Methylation of the 6β-hydroxypenicillanic acid (0.41 g, 1.90 mmol) with diazomethane in ethyl ether gave the methyl ester as an oil. Purification with a silicic acid column eluted with 1:4 Et$_2$O/CH$_2$Cl$_2$ gave 45b as a colorless oil, 0.12 g (27%); $R_f=0.48$ (1:4 Et$_2$O/CH$_2$Cl$_2$); $[\alpha]_D^{25}=+153°$ (c=1.30, CHCl$_3$); ir (film, cm$^{-1}$) 3420, 1785, 1740, 1440, 1290, 1210; nmr (DCCl$_3$, ppm) 5.65–5.58 (d, 1H, J=4), 5.30–5.05 (q, br, 1H, J=4 and 11), 4.50 (s, 1H), 3.80 (s, 3H), 3.35–3.15 (d, br, 1H, J=11), 1.70 (s, 3H), 1.55 (s, 3H).

Anal. Calcd for C$_9$H$_{13}$O$_4$NS (231.26): C, 47.25; H, 5.67; N, 6.06; S, 13.85. Found: C, 47.44; H, 5.79; N, 5.89; S, 13.96.

The bacteriostatic endpoint for the methyl ester in mcg. of active ester per ml is 32 for *Staphylococcus aureous* (10$^{-4}$ dilution) and 16 for K pneumoniae (10$^{-4}$ dilution).

Wittig reagents

Carbobenzyloxymethylenetriphenylphosphorane, benzoylethylenetriphenylphosphorane, and phenoxyacetylethylenetriphenylphosphorane were prepared by the action of sodium hydroxide on the readily accessible triphenylalkylphosphonium chlorides. Phenylacetylmethylenetriphenylphosphorane was made by the method of Bestmann and Arnason, ibid, using phenyl phenylacetate and methylenetriphenylphosphorane.

1-Chloro-3-phenoxyacetone

To a stirred solution of diazomethane (ca 6 g=0.141 mmol) in ethyl ether (400 ml) was added over 2 hours at 1°–3° phenoxyacetyl chloride (11.95 g=0.07 mole) dissolved in ethyl ether (50 ml). The mixture was stirred at the same temperature for two more hours and was allowed to stand overnight at room temperature. Then 5.5 N hydrochloric acid (25 ml, 0.137 moles) was added with stirring over 110 min. at 16°–20°. After the mixture was stirred for an additional 4 hours, the layers were separated and the ether layer was washed with three 80 ml portions of water and dried over anhydrous sodium sulfate. Removal of the solvent gave the crude product as a yellow oil, 13 g (100%); ir (film, cm$^{-1}$) 1740, 1595, 1495, 1240; nmr (DCCl$_3$, ppm) 7.40–6.70 (m, 5H), 4.60 (s, 2H), 4.25 (s, 2H). This product was used without purification to prepare phenoxyacetylmethyltriphenylphosphonium chloride.

Phenoxyacetylmethyltriphenylphosphonium Chloride

1-Chloro-3-phenoxyacetone (13 g, 0.07 mole) dissolved in 20 ml chloroform was mixed with a solution of triphenylphosphine (19.7 g, 1 eq) in 30 ml chloroform at room temperature. The mixture was swirled for 5 minutes and benzene (20 ml) was added. A white crystalline compound appeared when most of the solvents had been evaporated. The product was collected by suction and washed with benzene. Second and third crops were collected by evaporation of the washings. The total yield was 23 g (73%); sublimation without melting at 90°; ir (KBr, cm$^{-1}$), 3450–3280, 2770, 1720, 1595, 1585, 1485, 1435, 1220, 1110, 1030; nmr (DCCl$_3$, ppm) 8.20–6.80 (m, 22H), 5.30 (br, 2H).

Phenoxyacetylmethylenetriphenylphosphorane

Phenoxyacetylmethyltriphenylphosphonium chloride (10 g, 22.40 mmol) was suspended in 250 ml water with a few crystals of phenolphthalien added as an indicator. Sodium hydroxide (5%) was added dropwise until the vigorously stirred mixture turned pink. The white solid was collected, washed with water, and dried in a desicator, weight 9 g (98%); mp 127–128.5; ir (KBr, cm$^{-1}$) 1595, 1580, 1540, 1480, 1435, 1400, 1225, 1105, 1045, 870; nmr (DCCl$_3$, ppm) 7.90–6.90 (m, 21H), 4.53 (s, 2H).

Wittig reaction

6-OPA benzyl ester benzyl-6-oxopenicillanate was refluxed in benzene with 1.2 equivalents of each of the above Wittig reagents for 40 hours. The yellow solution turned dark brown. The resulting black oil from evaporation of solvent was fractionated with a silicic acid column eluted with 1:25 Et$_2$O/CH$_2$Cl$_2$. A brown oil containing the adduct was obtained. Treatment of the adduct in methylene chloride with activated charcoal and rechromatography on silicic acid eluted with 1:50 Et$_2$O/CH$_2$Cl$_2$ yielded a yellow, oily product.

Benzyl 6-benzoylmethylenepenicillanate

This compound was isolated as a yellow oil in 64% yield; R$_f$=0.75 (1:50 Et$_2$O/CH$_2$Cl$_2$); ir (film, cm$^{-1}$) 1770, 1740, 1690, 1635, 1595, 1450; nmr (DCCl$_3$, ppm) 8.07–7.30 (m, 11H), 6.12 (d, 1H, J=1), 5.22 (s, 2H), 4.60 (s, 1H), 1.60 (s, 3H), 1.45 (s, 3H).

Benzyl 6-phenoxyacetylmethylenepenicillanate

This compound was isolated as a yellow oil in 62% yield; R$_f$=0.65 (1:25 Et$_2$O/CH$_2$Cl$_2$); [α]$_D^{25}$=+279° (c=1.20, CHCl$_3$); ir (film, cm$^{-1}$) 1775, 1735, 1715, 1595, 1490; nmr (DCCl$_3$, ppm) 7.40–6.70 (m, 11H), 6.05 (d, 1H, J=1), 5.15 (s, 2H), 4.70 (s, 2H), 4.65 (s, 1H), 1.55 (s, 3H); 1.40 (s, 3H).

Anal. Calcd for C$_{24}$H$_{23}$NO$_5$S (437.51): C, 65.95; H, 5.30, N, 3.20; S, 7.32 Found: C, 65.77; H, 5.40; N, 3.31; S, 7.41.

Hydrogenation of Benzyl 6-benzoylmethylenepenicillanate

Benzyl 6-benzoylmethylenepenicillanate (0.92 g, 2.26 mmol) was hydrogenated in the presence of 1.6 g platinum oxide in 100 ml ethyl acetate for 10 hours at room temperature and 1 atm pressure. After filtration through celite cake, the filtrate was still brown in color owing to the colloidal platinum particles. It was treated with activated charcoal and evaporated to yield a yellow oil (0.75 g) which was fractionated with a silicic acid column eluted with 1:50 Et$_2$O/CH$_2$Cl$_2$ to give benzyl 6-benzoylmethylpenicillanate.

Benzyl 6-benzoylmethylpenicillanate

Early fractions from the column gave the major component which was shown by nmr to be a mixture of cis and trans isomers of benzyl 6-benzoylmethylpenicillanate (51c), weight 0.45 g (48.5%); R$_f$=0.45 (1:50 Et$_2$O/CH$_2$Cl$_2$). In an attempt to separate the cis and trans isomers, the yellow oil was rechromatographed on silicic acid eluted with 1:50 Et$_2$O/CH$_2$Cl$_2$ and the collected fractions were checked by nmr. Integrations showed that one early fraction had a cis/trans ratio of 2 to 1 and for a later fraction, it was 19:3. Nmr spectrum for a 19:7 cis/trans mixture (relative integration values are shown, ppm) 8.05–7.20 (m, 97, aromatic protons), 5.70 (d, 6.6, J=4.5, C-5 protons of the cis isomer), 5.20 (s, 17.5, benzylic protons), 5.10 (d, 2.4, J=1.5, C-5 proton of the trans isomer), 4.52 (s, 2.4, C-3 proton of the trans isomer), 4.48 (s, 6.6, C-3 proton of the cis isomer), 4.30–3.25 (m, 26, C-6 protons and protons to the ketone function), 1.60–1.40 (d over d, 54, gemdimethyl protons); ir (film, cm$^{-1}$) 1770, 1740, 1680, 1600, 1450.

Anal. Calcd for C$_{23}$H$_{23}$NO$_4$S (409.49): C, 67.50; H, 5.66; N, 3.42; S, 7.82. Found: C, 67.70; H, 5.71; N, 3.36; S, 7.76.

Benzyl 6-phenoxyacetylmethylpenicillanate

Benzyl 6-phenoxyacetylmethylenepenicillanate (2.65 g, 6.07 mmol) was hydrogenated in the presence of platinum oxide (4.3 g) in 200 ml ethyl acetate for 5 hours at room temperature and 1 atm. pressure. Colloidal platinum particles were removed by treating with activated charcoals as described in the preparation of benzyl 6-benzoylmethylpenicillanate. After separation with silicic acid column eluted with 1:10 Et$_2$O/CH$_2$Cl$_2$, three portions were collected. The first portion, as shown by nmr spectrum, was a mixture of cis/trans isomers of a ratio of 4 to 1; weight 0.75 g, 29% yield. The second portion was the pure cis isomer, weight 0.02 g, 3% of the total yield of the saturation products. The third portion was 2,2-dimethyl-3-carbobenzyloxy-6-phenoxyacetylmethyl-7-oxo-2,3,4,7-tetrahydro-1,4-thiazepine (52d), weight 0.20 g, 7.5% yield; ir (film, cm$^{-1}$) 3310, 1735, 1625, 1600, 1550–1500, 1200, 910; nmr (DCCl$_3$, ppm) 7.35–6.40 (m, 12H), 5.20 (s, 2H), 4.70 (s, 2H), 4.32–4.25 (d, 1H, J=5), 3.73–2.92 (q, 2H, J=16), 1.45 (s, 3H), 1.38 (s, 3H). The cis isomer, namely benzyl 6β-phenoxyacetylmethylpenicillanate is a pale yellow oil; R$_f$=0.75 (1:10 Et$_2$O/CH$_2$Cl$_2$); [α]$_D^{25}$=+148° (c=0.46, CHCl$_3$); ir (film, cm$^{-1}$) 1770, 1735, 1595, 1490; nmr (DCCl$_3$, ppm) 7.50–6.80 (m, 10H), 5.65 (d, 1H, J=4.2), 5.20 (s, 2H), 4.60 (s, 2H), 4.45 (s, 1H), 4.30–3.85 (m, 1H), 3.25–3.12 (d, 2H, J=8), 1.58 (s, 3H), 1.42 (s, 3H).

Anal. Calcd for C$_{24}$H$_{25}$NO$_5$S (439.52): C, 65.60; H, 5.74 N, 3.19; S, 7.28. Found: C, 65.40; H, 5.90; N, 3.12; S, 7.40.

6β-Phenoxyacetylmethylpenicillanic acid

Hydrogenolysis of benzyl 6-phenoxyacetylmethylpenicillanate to give 6β-phenoxyacetylmethylpenicillanic acid was carried out as described for the preparation of 6β-phenoxyacetoxypenicillanic acid. Starting with a sample of benzyl 6β-phenoxyacetylmethylpenicillanate (0.35 g, 0.80 mmol) containing 8:1 cis/trans isomers, the product obtained was pure cis compound as shown by nmr spectrum. The free acid when isolated can be purified by recrystallisation. Thus the acid was first dissolved in methylene chloride which is then replaced by benzene. The benzene solution is chilled to give 0.12 g (43%) white crystals; mp 101.5°–102°; [α]$_D^{25}$=+217° (c=0.62 CHCl$_3$); ir (KBr, cm$^{-1}$) 3440, 1785, 1765, 1750, 1730, 1720, 1700, 1595, 1490, 1225; nmr (DCCl$_3$, ppm) 11.15 (s, 1H), 7.50–6.85 (m, 5H), 5.65 (d, 1H, J=4.5), 4.65 (s, 2H), 4.50 (s, 1H), 4.30–3.95 (m, 1H), 3.35–3.20 (d, 2H, J=8), 1.65 (d, 6H).

Anal. Calcd for C$_{17}$H$_{19}$NO$_5$S (349.39): C, 58.50; H, 5.49; N, 4.02; S, 9.16. Found: C, 58.73; H, 5.47; N, 3.93; S, 9.11.

The bacteriostatic endpoint in mcg of active material per ml is 1 for *D pneumoniae* (5% serum), 2 for *Streptococcus pyogenes* (5% serum) and 32 for *Staphylococcus aureus* (10$^{-4}$ dilution).

We claim:

1. An oxygen analog of 6-aminopenicillanic acid having the formula:

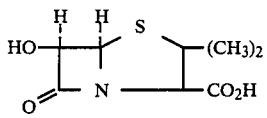

2. Oxygen analogs of 6-aminopenicillanic acid having the formula:

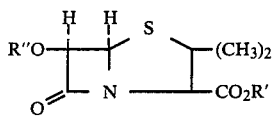

where R' is hydrogen or a pharmaceutically acceptable group and R" is an acyl group.

3. The oxygen analog of claim 2 where R" is an acyl group selected from the group of aryl acetyl, aryloxy acetyl, aryl carbonyl, aryloxy carbonyl alkyl sulfonyl and aryl sulfonyl groups.

4. The oxygen analog of claim 2 where R" is selected from the group consisting of formyl, acetyl, phenylacetyl, phenoxyacetyl, carbomethoxy, carbobenzyloxy, p-nitrocarbobenzyloxy, carbophenoxy, p-chlorocarbophenoxy, 2,6-dimethoxybenzoyl, α-carboxyphenylacetyl, α-aminophenylacetyl, tyrosyl, carbo-β,β,β-trichloroethoxy, methanesulfonyl, benzylsulfonyl, p-chlorobenzylsulfonyl, phenylsulfonyl, p-aminophenylsulfonyl and N,N-pentamethylenesulfonyl.

5. The oxygen analog of claim 3 where R" is phenylacetyl.

6. The oxygen analog of claim 3 where R" is phenoxyacetyl.

7. The oxygen analog of claim 3 where R" is 2,6-dimethylbenzoyl.

8. The oxygen analog of claim 4 where R' is selected from the group of alkyl, cycloalkyl, aryl, alkaryl, aralkyl, phenacyl, salts and organo silicon groups.

9. The oxygen analog of claim 8 where R' is methyl.

10. The oxygen analog of claim 8 where R' is benzyl.

11. The oxygen analog of claim 8 where R' is p-methoxyphenacyl.

12. The oxygen analog of claim 8 where R' is 2,6-dimethylphenacyl.

13. A process for the formation of an oxygen analog of 6-aminopenicillanic acid, said process comprising subjecting an ester of 6-oxopenicillanate of the formula:

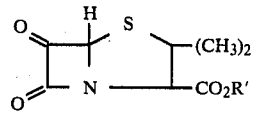

where R' is a pharmaceutically acceptable group to the action of a reducing agent.

14. The process of claim 13 where the reducing agent is borohydride.

15. The process of claim 14 where the borohydride is potassium borohydride.

16. The process of claim 15 where R' is a pharmaceutically acceptable, readily removable blocking group.

17. The process of claim 13 where R' is selected from the group consisting of alkyl, cycloalkyl, aryl, alkaryl, aralkyl, salts and organo silicon groups.

18. The process of claim 13 where R' is methyl.

19. The process of claim 13 where R' is benzyl.

20. The process of claim 13 where R' is methoxyphenacyl.

21. The process of claim 13 including the step of acylating the analog formed by reducing the 6-oxopenicillanate to form a compound corresponding to the formula:

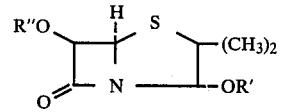

where R' is as defined above and R" is an acyl group.

22. The process of claim 21 where R" is selected from the group consisting of aryl acetyl, aryloxy acetyl, aryl carbonyl, aryloxy carbonyl alkyl sulfonyl and aryl sulfonyl groups.

23. The process of claim 22 where R" is phenylacetyl.

24. The process of claim 22 where R" is phenoxyacetyl.

25. The process of claim 22 where R" is 2,6-dimethylbenzoyl.

26. The process of claim 21 where R" is selected from the group consisting of formyl, acetyl, phenylacetyl, phenoxyacetyl, carbomethoxy, carbobenzyloxy, p-nitrocarbobenzyloxy, carbophenoxy, p-chlorocarbophenoxy, 2,6-dimethoxybenzoyl, α-carboxyphenylacetyl, α-aminophenylacetyl, tyrosyl, carbo-β,β,β-trichloroethoxy, methanesulfonyl, benzylsulfonyl, p-chlorobenzylsulfonyl, phenylsulfonyl, p-aminophenylsulfonyl and N,N-pentamethylenesulfonyl.

27. The process of claim 21 where R" is a sulfonyl radical.

28. The process of claim 17 including the step of hydrogenolysis to form the free acid.

29. The process of claim 28 where hydrogenolysis is by passage over a palladium catalyst.

30. The process of claim 29 including the step of esterifying the free acid.

31. A compound having the formula:

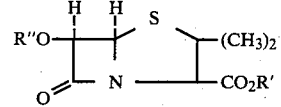

wherein R' is hydrogen or a pharmaceutically acceptable group and R" is hydrogen or an acyl group.
32. The process of claim 13 including the step of acylating the analog formed by reducing the 6-oxopenicillanate to form a compound having the formula:
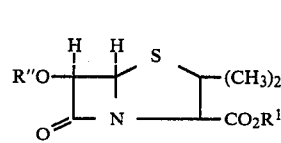
wherein R' is as defined above and R" is hydrogen or an acyl group.
* * * * *